(12) United States Patent
Brehm (10) Patent No.: US 10,543,063 B2
(45) Date of Patent: Jan. 28, 2020

(54) DENTAL PROSTHESIS ARRANGEMENT

(71) Applicant: bredent GmbH & Co. KG, Senden (DE)

(72) Inventor: Peter Brehm, Senden (DE)

(73) Assignee: bredent GmbH & Co. KG, Senden (DE)

(*) Notice: Subject to any disclaimer, the term of this patent is extended or adjusted under 35 U.S.C. 154(b) by 0 days.

(21) Appl. No.: 15/107,180

(22) PCT Filed: Dec. 16, 2014

(86) PCT No.: PCT/EP2014/078054
§ 371 (c)(1),
(2) Date: Jun. 22, 2016

(87) PCT Pub. No.: WO2015/097024
PCT Pub. Date: Jul. 2, 2015

(65) Prior Publication Data
US 2016/0374782 A1    Dec. 29, 2016

(30) Foreign Application Priority Data
Dec. 23, 2013 (DE) .......................... 10 2013 114 779

(51) Int. Cl.
*A61C 8/00* (2006.01)

(52) U.S. Cl.
CPC .......... *A61C 8/0068* (2013.01); *A61C 8/0054* (2013.01); *A61C 8/0056* (2013.01);
(Continued)

(58) Field of Classification Search
CPC ... A61C 8/0068; A61C 8/0054; A61C 8/0056; A61C 8/0057; A61C 8/0062; A61C 8/0066
See application file for complete search history.

(56) References Cited

U.S. PATENT DOCUMENTS 2,644,231 A * 7/1953 Brennan ................... A61C 5/80
                                                     433/173
2,866,285 A * 12/1958 Gerber ............... A61C 13/2656
                                                     433/219
(Continued)

FOREIGN PATENT DOCUMENTS

DE    10 2004 051 437 A1    6/2005
DE    10 2004 044 888 A1    3/2006
WO         02/24104 A1      3/2002

OTHER PUBLICATIONS

International Search Report of PCT/EP2014/078054, dated Feb. 19, 2015.

*Primary Examiner* — Cris L. Rodriguez
*Assistant Examiner* — Hao D Mai
(74) *Attorney, Agent, or Firm* — Collard & Roe, P.C.

(57) ABSTRACT

A dental prosthesis arrangement includes a lower part assigned to a jaw implant and an upper part assigned to a superstructure. The lower part engages in the upper part along a central axis. The lower part is supported against the upper part at several contact faces. The lower part and the upper part are connected releasably to each other via a securing device which provides a retaining force against axial withdrawal of the upper part from the lower part. A first radially inwardly directed structure is provided on the lower part and a second radially outwardly directed structure is provided on the upper part for receiving a holding element that provides the retaining force. A fastener passing through the upper part and connected to the lower part can alternatively fix the upper part to the lower part.

12 Claims, 6 Drawing Sheets

(52) U.S. Cl.
CPC .......... *A61C 8/0057* (2013.01); *A61C 8/0062* (2013.01); *A61C 8/0066* (2013.01)

(56) References Cited

U.S. PATENT DOCUMENTS

| | | | | |
|---|---|---|---|---|
| 4,447,210 | A * | 5/1984 | Hidaka | A61C 8/0086 433/169 |
| 4,604,060 | A * | 8/1986 | Weissman | A61C 13/30 433/221 |
| 4,681,542 | A * | 7/1987 | Baum | A61C 13/00 433/172 |
| 5,033,962 | A * | 7/1991 | Scatena | A61C 8/005 433/169 |
| 5,049,073 | A * | 9/1991 | Lauks | A61C 8/0018 433/169 |
| 5,106,299 | A * | 4/1992 | Ghalili | A61C 8/0048 433/172 |
| 5,350,302 | A * | 9/1994 | Marlin | A61C 8/0048 433/173 |
| 5,362,235 | A * | 11/1994 | Daftary | A61C 8/0048 433/172 |
| 5,620,323 | A * | 4/1997 | Bressman | A61C 8/0022 433/174 |
| 5,660,545 | A * | 8/1997 | Bailey | A61C 8/005 433/173 |
| 5,667,384 | A * | 9/1997 | Sutter | A61C 8/0048 433/172 |
| 5,863,200 | A * | 1/1999 | Hamada | A61C 8/0048 433/173 |
| 5,873,721 | A * | 2/1999 | Willoughby | A61C 8/0001 433/172 |
| 5,897,320 | A * | 4/1999 | Gittleman | A61C 3/16 433/172 |
| 5,915,968 | A * | 6/1999 | Kirsch | A61C 8/0018 433/169 |
| 5,997,299 | A | 12/1999 | Unger | |
| 6,273,721 | B1 * | 8/2001 | Valen | A61C 8/0022 433/174 |
| 6,299,447 | B1 | 10/2001 | Zuest et al. | |
| 6,663,388 | B1 | 12/2003 | Schär et al. | |
| 6,716,030 | B1 * | 4/2004 | Bulard | A61C 8/0048 433/174 |
| 6,848,908 | B2 * | 2/2005 | Bjorn | A61C 8/005 433/172 |
| 7,264,469 | B2 * | 9/2007 | Abarno | A61C 1/084 433/173 |
| 7,866,981 | B2 * | 1/2011 | Brajnovic | A61C 8/0034 433/173 |
| 8,348,668 | B2 * | 1/2013 | Lauridsen | A61C 8/0053 433/173 |
| 2002/0177103 | A1 * | 11/2002 | Pelak | A61C 8/0048 433/173 |
| 2009/0117520 | A1 * | 5/2009 | Kikuchi | A61C 8/005 433/174 |
| 2009/0136899 | A1 * | 5/2009 | Porter | A61C 8/0001 433/174 |
| 2012/0264082 | A1 * | 10/2012 | Segura | A61C 8/0048 433/174 |
| 2013/0143178 | A1 * | 6/2013 | van Ophuysen | A61C 8/0054 433/173 |
| 2013/0288201 | A1 * | 10/2013 | Zhao | A61C 8/001 433/174 |
| 2014/0141387 | A1 * | 5/2014 | Kikuchi | A61C 13/235 433/174 |

* cited by examiner

DENTAL PROSTHESIS ARRANGEMENT

CROSS REFERENCE TO RELATED APPLICATIONS

This application is the National Stage of PCT/EP2014/078054 filed on Dec. 16, 2014, which claims priority under 35 U.S.C. § 119 of German Application No. 10 2013 114 779.8 filed on Dec. 23, 2013, the disclosures of which are incorporated by reference. The international application under PCT article 21(2) was not published in English.

BACKGROUND OF THE INVENTION

1. Field of the Invention

The invention relates to a dental prosthesis arrangement.

2. Description of the Related Art

It is known that dental prostheses are used to replace missing teeth of a set of teeth. In this regard, dental prosthesis arrangements are used that have a superstructure anchored in the jawbone by way of a jaw implant. It is advantageous that a cohesive superstructure can be provided by way of multiple jaw implants, for placement of multiple adjacent teeth or also all the teeth of a jaw.

From the general state of the art, it is known to carry out attachment of a dental prosthesis superstructure on a jaw implant by means of cement. Such attachment leads to a firmly seated tooth replacement. However, cementing proves to be disadvantageous because in particular, periodontal cleaning of the tooth replacement can be carried out only with great difficulty or not at all. In this regard, particularly attention must be paid to the fact that the formation of what are called biofilms on hard surfaces, such as, for example, on implants, in the oral cavity of a prosthesis wearer, is unavoidable. The bacteria contained in the biofilm are frequently triggers of infectious diseases, which have increasingly been the focus of medical and dental research recently. For example, it has been shown that about 60% to 70% of all infectious diseases of the human body are associated with biofilms. In addition, there is the complicating factor that biofilm bacteria are furthermore situated outside of the reach of the immune defense of the human body, and that they can frequently be transferred, without problems, to other individuals, in the form of pathogenic germs. Similar to periodontal pockets of natural teeth, prophylactic care is necessary for peri-implant pockets, as well.

Peri-implant inflammations develop on the same basis as periodontal inflammations. For example, implants already demonstrate subgingival biofilms within two weeks after their exposure. The microorganisms found in them actually have a greater pathological potential, in part, than the biofilms present on the root surfaces. It has been shown that these pathological germs demonstrate a great affinity to titanium, which is frequently used in the production of implants. Studies have shown that over half of all implants are colonized with germs. Subgingival biofilms consequently represent a microbial depot with great infectious and antigenic potency, penetrate into the tissue through the permeable periodontal or peri-implant junctional epithelia, and get into the blood stream.

In order to further reduce or prevent the risks of disease associated with these germs, such as cardiovascular diseases, arteriosclerosis, diabetes or cancer, for example, mechanical removal of the biofilm is absolutely necessary also for wearers of tooth replacements. The replacement of periodontally pre-damaged teeth with osseo-integrated implants requires regular follow-up care to monitor biofilms building up on the implant. However, in the case of old people, who frequently suffer from concomitant circumstances such as dementia and physical ailments, this frequently cannot be carried out. Consequently, the implant-supported tooth replacement must be adapted to these symptoms.

It is therefore necessary to adapt dental prosthesis arrangements, taking into consideration the demographic development of society, to the effect that removable or conditionally removable dental prostheses are made available in place of firmly fixed dental prostheses.

Various systems for releasable attachment of a prosthesis to a substructure with one or more jaw implants are known for being able to remove the dental prosthesis superstructure without damage or destruction. In this regard, as has already been mentioned, a prosthesis that can be removed only by the treating dentist, if necessary using a tool, is referred to as being conditionally removable, and a prosthesis that can be released and replaced also by the wearer of the prosthesis himself/herself, without a tool, is referred to as being removable. Such conditionally removable or removable prostheses simultaneously avoid the stated problems of cementing.

In U.S. Pat. No. 6,299,447 B1, a connection type in the form of snaps is described, in which a cap that is open toward the jaw is cast into a prosthesis, and on the jaw implant, a post that is widened at the upper end with a radial bulge, in bollard-like manner, projects away from the jaw. With the interposition of a ring having a radially convex-curved wall, the cap can be reversibly snapped onto the bollard and pulled off it, by overcoming a holding force. Such arrangements are particularly advantageous for full dentures and can also be removed and replaced by the wearer of the prosthesis.

In U.S. Pat. No. 5,667,384, a dental prosthesis arrangement is described, in which a head screw is firmly screwed onto an implant. A recess in the cap of a removable prosthesis engages over the head screw, and an attachment screw that essentially leads radially through the cap supports itself on the screw head, on the bottom, with its conical surface, and presses the cap in the direction of the jaw implant, where prosthesis and implant support themselves against one another on a conical sealing surface. The attachment screw simultaneously pulls the opposite inner wall laterally against the screw head. In place of a head screw as part of a multi-part implant and as a counter-surface to the conical surface of the attachment screw, a sleeve attached to the jaw implant, having a conical outer wall, which forms a contact surface with a conical inner wall of the cap, and having a circumferential groove, can form a counter-surface to the attachment screw. The prosthesis can be removed from the jaw by releasing the attachment screw in the dentist's office, and this is referred to as conditionally removable.

In DE 10 2004 051 437 A1, a double crown is described, in which a primary crown possesses a cylindrical outer surface, and a secondary crown can be pushed over the primary crown with a suitably shaped cylindrical recess. The primary crown has a horizontal groove in its cylinder mantle surface, into which an elastic pin of the secondary crown engages and secures the secondary crown to prevent it from being pulled off the primary crown, with a holding force that must be overcome to pull off the primary crown.

From U.S. Pat. No. 2,866,285 A, an apparatus for releasable connection of an artificial tooth is known. In this regard, a cylindrical region part of a depression in the interior of a hollow cap is structured to be axially adjacent to and with a smaller diameter with regard to a coaxial cylinder part, wherein the coaxial cylinder part is formed on an inner surface. The coaxial cylinder part is connected with a flange that serves as a stop with regard to the cap. During affixation of the cap, a ring-shaped element is pressed into a furrow, so that at the same time, the cap is pressed against the flange.

SUMMARY OF THE INVENTION

The present invention is based on the task of indicating a dental prosthesis arrangement having a reversibly removable or conditionally removable prosthesis over one or more jaw implants.

This task is accomplished by means of the characteristics described herein. Further advantageous embodiments of the invention are also described herein. These can be combined with one another in technologically reasonable manner. The description, particularly in combination with the drawing and claims, characterizes and specifies the invention.

According to the invention, a dental prosthesis arrangement for connection of at least one jaw implant with a superstructure, which are connected with one another in a connection segment, by way of a lower part assigned to the jaw implant and an upper part assigned to the superstructure, is created. The lower part engages into the upper part in the connection segment, along a center axis. The lower part is supported against the upper part at multiple contact surfaces. The lower part and the upper part are releasably connected with one another by way of an attachment means that brings about a holding force that prevents the upper part from being axially pulled off the lower part, wherein different attachment means can be selected, in that a first structure directed radially inward is provided on the lower part, and a second structure directed radially outward is provided on the upper part, for accommodation of a holding element, and the parts can be fixed in place by means of at least one further element that passes through the upper part and stands in connection with the lower part.

For the further element, a first opening for accommodation of a transversal screw connection can be provided on the upper part and/or a second opening for accommodation of a latch element can be provided on the upper part.

Accordingly, a dental prosthesis arrangement is made available, in which releasable attachment between a lower part and an upper part is possible. In this regard, the lower part can be introduced into a jaw implant, and the upper part can be assigned to a superstructure, for example to a dental prosthesis arrangement. In contrast to the releasable connection structures known from the state of the art, an attachment means is made available, according to the invention, in which different types of attachment can be selected. This makes it possible to create a plurality of different dental prosthesis arrangements, which ensure a releasable connection in different ways, but without having to create a separate connection structure for each connection type. Accordingly, it is provided as a first attachment possibility to create two structures that lie opposite one another, between which a holding element can be provided. The first connection type therefore relates to an attachment possibility that is created in the interior between the upper part and the lower part. As a second attachment possibility, a transversal screw connection is provided, which is undertaken through a first opening on the upper part. The third attachment possibility comprises a latch element that can project through a second opening on the upper part. Because all the structures and/or openings are already provided on the superstructure according to the invention, one of the said attachment possibilities can be selected, depending on the application case. The other attachment possibilities, not provided in the corresponding application case, can be closed off by means of an adhesive or something similar, for example, if they are provided in the form of openings on the outside of the upper part. The structured disposed in the interior, between the upper part and the lower part, can also remain there without a holding element. According to the invention, a flexible, universally usable attachment means is consequently created, which can be advantageously used, in the case of the dental prosthesis arrangement, for a releasable connection between superstructure and jaw implant.

According to an embodiment of the invention, the first structure is configured as a ring-shaped groove, the second structure as a recess, and the holding element as an elastically deformable ring.

Here, the connection between the upper part and the lower part is formed by a ring that can engage both into the ring-shaped groove and into the recess. Because of the elastic deformability of the ring, it is therefore possible to join the two parts together in order to achieve seating of the superstructure on the jaw implant.

According to a further embodiment of the invention, the ring comprises a rubber-elastic and/or elastically compressible material, and can be elastically deformed radially.

Accordingly, multiple different holding elements, for example, can be provided in a dental prosthesis system having such a dental prosthesis arrangement, which elements are designed in such a manner that they bring about different holding forces, while otherwise having the same properties. The different holding elements can differ, for example, in terms of cross-section and/or material, for example elastomer material having different Shore hardness values. In the case of removable prostheses, a holding force appropriate for the respective user can be adjusted by means of the selection of a corresponding holding element.

According to a further embodiment of the invention, the latch element comprises a pin-shaped segment that engages into the groove of the lower part with a latch tip in an engagement position, or runs in the groove tangentially with reference to the center axis of the lower part.

Accordingly, an attachment means is created, which is accessible both to the user and also to a treating dentist, and can be activated manually or by means of a tool. In this regard, the attachment means can be configured as a latch element that particularly ensures a hold between upper part and lower part, as an insertion latch. A bracket-form locking mechanism is also possible.

The latch element can be configured as an insertion latch, sliding latch, pivot latch, rotating latch or U-shaped bracket locking mechanism.

Resilient insertion latches particularly allow the wearer of the dental prosthesis arrangement to perform independent removal, and, in this regard, the reset means ensures a reliable hold while the prosthesis is worn.

According to a further embodiment of the invention, the first opening is configured cylindrically and provided with an inside thread into which a screw having an outside thread can be introduced to form the transversal screw connection.

Accordingly, it is possible to also provide the dental prosthesis arrangement according to the invention by means of a transversal screw connection known from the state of the art.

According to a further embodiment of the invention, the upper part is closed on its top side facing away from the jaw implant.

Accordingly, the top side is structured in the form of a cap onto which the dental prosthesis can subsequently be affixed.

According to a further embodiment of the invention, the upper part is provided with a third opening for accommodation of an occlusal screw connection on its top side facing away from the jaw implant.

In this alternative, the upper part is not structured as a cap, but rather is open toward the top. A screw can be introduced through this opening, in the axial direction, which screw makes it possible to connect upper part and lower part with one another. Accordingly, however, it is necessary, after application of the prosthesis, to close off the passage opening of the screw by means of a suitable closure material, so that removal of the closure material is necessary to remove the dental prosthesis arrangement.

According to a further embodiment of the invention, the third opening is surrounded by a cylindrical extension, which faces away from the jaw implant.

The cylindrical extension can be used as a superstructure element for the subsequent dental prosthesis.

According to a further embodiment, the cylindrical extension is formed in the direction of the center axis.

According to this embodiment, a straight design of the upper part takes place, onto which the dental prosthesis is set.

According to a further embodiment, the cylindrical extension is angled relative to the center axis.

Accordingly, it is possible to provide the passage opening for the occlusal screw connection at a location of the dental prosthesis that is not subject to any great mechanical stress, for example, particularly resulting from chewing forces when wearing the prosthesis. Accordingly, almost any desired variation in the location of the passage opening is possible by means of the selection of the corresponding angling or positioning of the angled-away cylindrical extension.

According to a further embodiment, the cylindrical extension and the upper part are structured in one piece or can be welded to one another.

Particularly in the case of angled cylindrical extensions, the connection with the upper part along with the screw can take place by means of a welded connection. Accordingly, it is not necessary, for example, to provide an extensive cavity above the center axis, which projects downward, in order to be able to produce the occlusal screw connection. Accordingly, a dental prosthesis arrangement that has a compact shape is provided.

According to a further embodiment of the invention, the holding element, the latch element, and the transversal screw connection, as well as the occlusal screw connection, bring about an axial press-down force against a contact surface on the end of the connection segment that faces the jaw implant.

The axial press-down force particularly prevents gaps from being able to form between the upper part and the lower part, wherein contaminants can be removed in this gap only with difficulty. Accordingly, a hermetic seal between upper part and lower part is achieved on the basis of the axial press-down force.

It is possible to overcome the holding force without destruction of upper part and lower part, in order to release the connection between upper part and lower part.

Accordingly, the holding elements for making the connection between upper part and lower part must be selected accordingly.

In addition, it is also provided that the holding force can be overcome without destruction of the holding element.

BRIEF DESCRIPTION OF THE DRAWINGS

In the following, some exemplary embodiments will be explained in greater detail, using the drawing. This shows.

DETAILED DESCRIPTION OF THE PREFERRED EMBODIMENTS

In the figures, components that are the same or have the same functional effect are provided with the same reference symbols.

Figure 1:
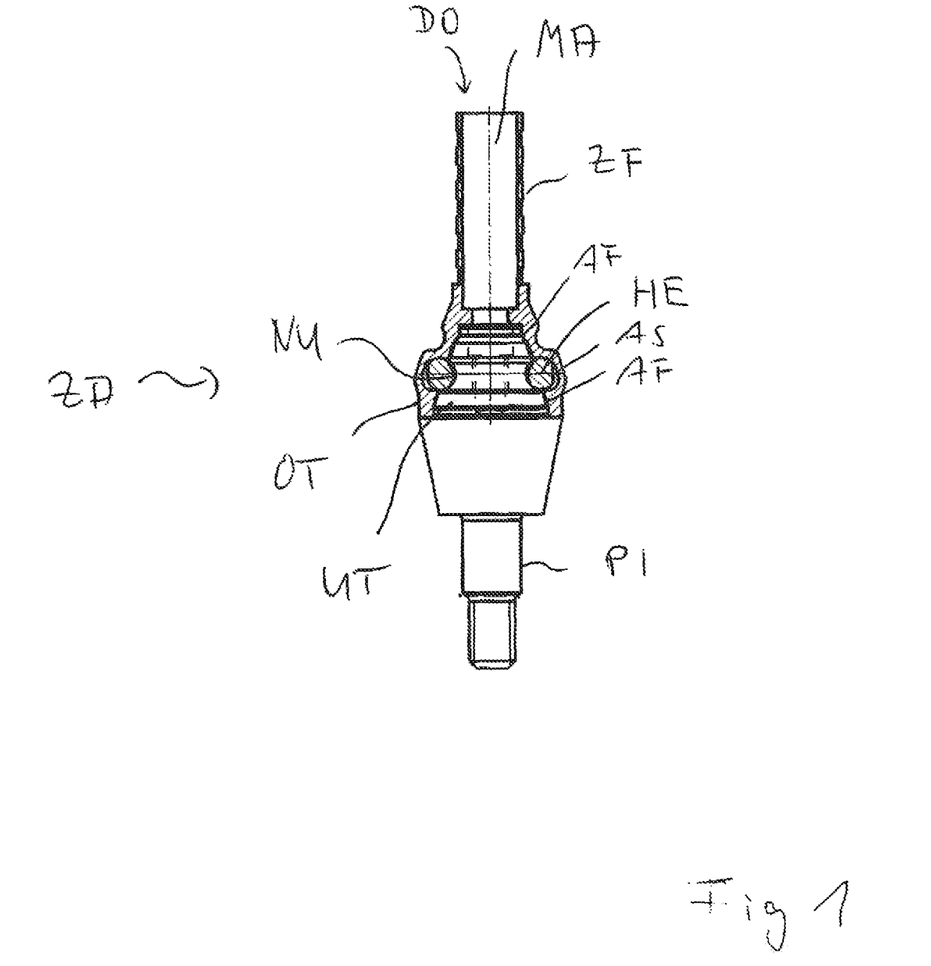
FIG. 1 a side view, partly in section, of a first embodiment of a dental prosthesis arrangement according to the invention, FIG. 2 a further side view of the dental prosthesis arrangement according to FIG. 1, FIG. 3 a further side view of the embodiment according to FIG. 1, FIG. 4(A) a further side view according to the embodiment according to FIG. 1, FIG. 4(B) a top view, partly in section, of the embodiment according to FIG. 4(A), FIG. 5 a further side view of the embodiment according to FIG. 1, and FIG. 6 a side view, partly in section, of a further embodiment.

In FIG. 1, a first embodiment of the dental prosthesis arrangement ZA according to the invention is shown schematically in a side representation, partly in section. A lower part UT is applied to a jaw implant, indicated schematically with the reference symbol PI, which part is covered by an upper part OT. The upper part OT can be used as a superstructure body for a dental prosthesis not shown in FIG. 1. The upper part OT and the lower part UT together form a connection segment VA, so that the lower part assigned to the jaw implant PI and the upper part assigned to the superstructure are connected with one another. The lower part UT engages into the upper part OT along a center axis MA. The lower part UT is supported against the upper part OT at multiple contact surfaces AF. The lower part UT and the upper part OT are releasably connected with one another by way of an attachment means that brings about a holding force to prevent the upper part OT from being axially pulled off the lower part UT.

According to the invention, multiple different attachment means can be selected, which will be explained hereinafter, making reference to the different embodiments described below. In FIG. 1, only one embodiment of the attachment means is shown for the sake of simplicity. In the example shown in FIG. 1, the attachment means is formed on the lower part UT by means of a first structure and on the upper part OT by means of a second structure, which structures jointly accommodate a holding element HE. The first structure is directed radially inward on the lower part UT and configured in the form of a groove NU. The second structure is directed radially outward on the upper part OT and configured in the form of a recess AS. In the cavity created between the groove NU and the recess AS, space is therefore created for accommodating the holding element HE. It is advantageous if the recess AS and the groove NU are configured along the complete circumference on the lower part UT and on the upper part OT. Accordingly, it is possible to configure the holding element HE in the form of a ring, wherein, however, it is not excluded to form the corresponding structures, at least in part, on the inside or outside of the lower part or upper part.

It is advantageous if the ring, as a holding element HE, comprises an elastic or elastically compressible material, and it should be radially elastically deformable, so that the ring can be set into the groove NU over the lower part UT. Then, the upper part OT would be guided over the elastically deformable ring as a holding element HE during assembly, so that on the basis of the deformation of the ring, reliable fixation in place of the lower part UT and the upper part OT occurs. In this regard, it must be possible to overcome the holding force caused by the holding element HE without destruction of upper part OT and lower part UT, in order to release the connection between upper part OT and lower part UT. It is also provided that the holding force can be overcome without destruction of the holding element HE itself.

Figure 6:
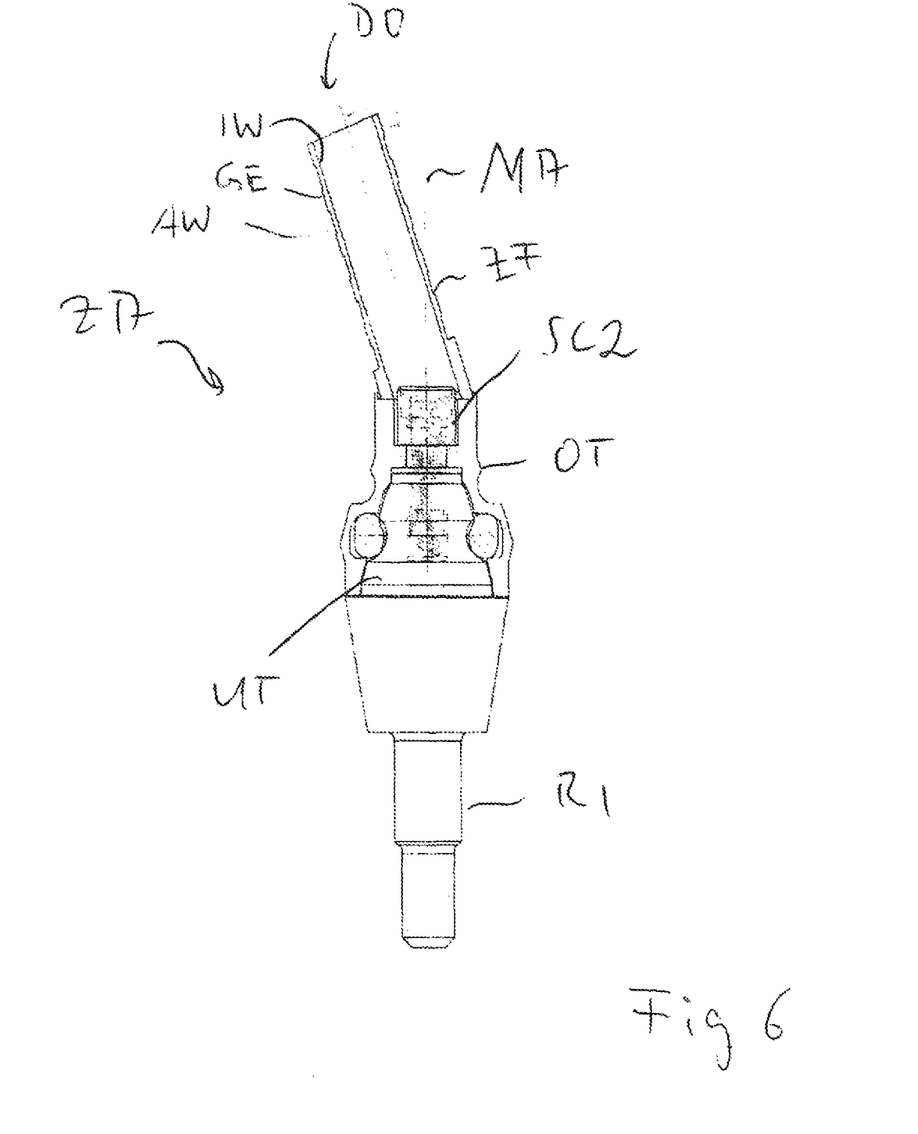

The holding ring HR as a holding element, which lies in the grooves NO and NU in the assembled state and brings about the holding force to prevent pull-off, can particularly consist of a plastic, which can also be understood to be an elastomer or a rubber material. Preferably, the groove NO in the upper part has a greater radial depth relative to the approximately conical surface KO than the groove NU does relative to the conical surface KU. Then, it is advantageous if the holding ring HR, in the state of the dental prosthesis arrangement in which the upper part is released from the lower part, lies in the groove NO of the upper part, as shown in FIG. 6, and can thereby be replaced outside of the mouth of the prosthesis wearer, if necessary, for example in order to be able to insert a new holding ring in the case of wear of the holding ring HR after the prosthesis body has been repeatedly reversibly set onto and released from of the implants, or in order to perform a comparison of different holding rings, one after the other, when trying out a holding force appropriate for the user.

The holding force brought about by the ring as a holding element HE in the preceding examples can be designed both in a range for a removable prosthesis, with more frequent insertion and removal by the user himself/herself, and also for a conditionally removable prosthesis, with a typically greater holding force.

The ring as a holding element HE can typically be configured also for a permanent connection of upper part OT and lower part UT, by means of configuration of its string cross-section and/or material in connection with the cross-sections of the groove NU and of the recess AS, and for this purpose, it can also be provided that although the connection can be released in a dentist's office, the ring might be destroyed when doing so.

It is also possible to configure the ring, as a holding element HE, with non-round string cross-sections, wherein the ring can have a V-shaped string cross-section with two shanks, for example, which are pressed elastically toward one another when the upper part OT is set onto the lower part UT, and automatically are pressed apart again when the groove NU is reached. In this variant, release of the connection of the upper part OT from the lower part UT has the result that removal can take place only with increased force and typically with destruction of the ring as the holding element HE. The string cross-section of the holding ring does not have to remain the same over the entire circumference, but rather can be present only on multiple circumference segments.

A further variant contains a wedge-shaped string cross-section of the ring as the holding element HE, in which a wedge tip is disposed facing away from the jaw-side end of the implant, and thereby an increased holding force to prevent the upper part OT from being pulled off the lower part UT exists. Depending on the configuration of the string cross-section and the selection of the material of the holding ring in detail, lifting of the upper part OT from the lower part UT can take place with destruction of the ring as the holding element HE or while maintaining it.

It is advantageous if the string cross-sections of the ring as the holding element HE particularly bring about asymmetry of the forces between setting of the upper part OT onto the lower part UT and pulling of the upper part OT off the lower part UT, in the direction of the center axis MA.

Figure 2:
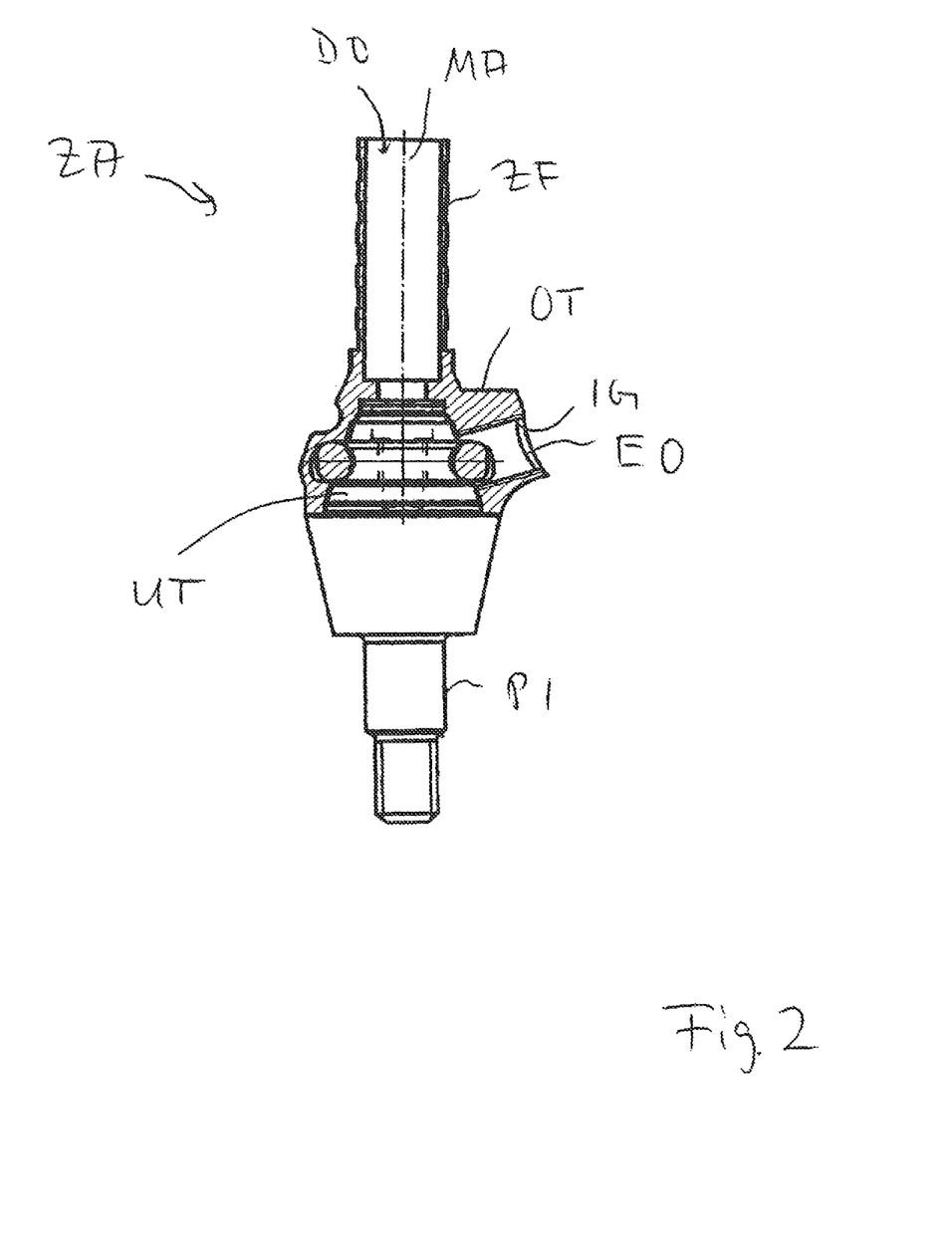

A further embodiment of the invention is shown in FIG. 2. FIG. 2 can be, for example, a representation that corresponds to a representation of the dental prosthesis arrangement ZA from FIG. 1, rotated along the center axis MA. In addition to the attachment means already created by means of the holding element HE, according to FIG. 2 a first opening EO is provided, which passes through the upper part. When a dental prosthesis is assembled, the possibility now exists to either use the attachment by means of the holding element HE, as shown in FIG. 2. Also, attachment of the lower part UT to the upper part OT can take place by way of the first opening EO, wherein the first opening EO is preferably configured to be cylindrical for this purpose, and is provided with an inside thread IG.

Figure 3:
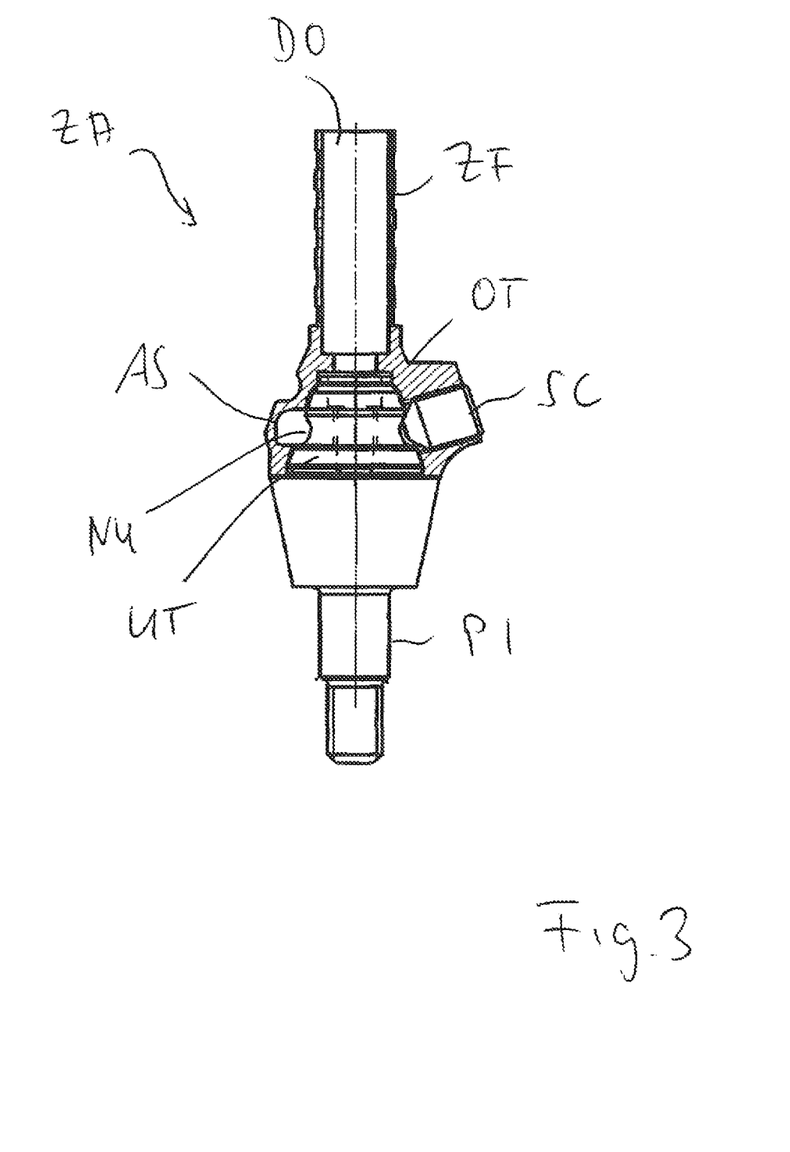

Making reference to FIG. 3, it is shown that a screw SC, for example one configured as a headless screw, can be introduced into the first opening EO, wherein preferably, an outside thread of the screw SC is brought into engagement with the inside thread IG on the cylindrical inner wall of the first opening EO. If the holding element HE is now not used, the screw SC can be brought into engagement with the groove NU of the lower part UT, so that reliable attachment of the lower part UT to the upper part OT takes place. Accordingly, the screw SC is used to form a transversal screw connection.

The dental prosthesis arrangement ZA therefore has alternative attachment possibilities, which can be used optionally. Accordingly, if the treating dentist or the wearer of the dental prosthesis decides in favor of a transversal screw connection, the embodiment according to FIG. 3 will be selected. If the holder of the upper part OT is supposed to be formed by way of the ring-shaped holding element HE, the embodiment according to FIG. 1 would be used. In this case, the first opening EO can also be sealed by means of a closure mass, if this opening will not be used later. Likewise, it is possible to introduce a blind screw, for example, that does not project all the way to the holding element HE in place of the screw SC, so that later, it would still be possible to use the transversal screw connection.

Figure 4A:
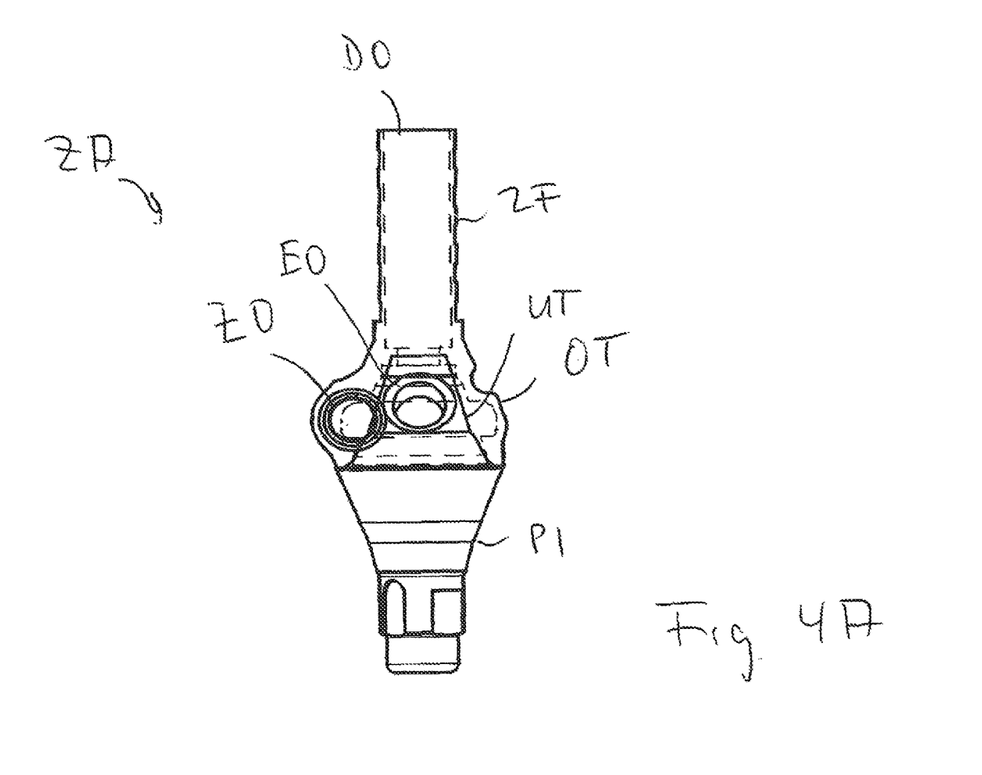

A further embodiment of the invention is shown by making reference to FIG. 4(A). Here, a latch element RE is passed through the upper part OT in place of a transversal screw connection. The latch element, as shown in FIG. 4(A), can run approximately tangentially with reference to the center axis of the lower part UT, in the groove NU that was already described in connection with FIG. 1. Accordingly, in an engagement position, a pin-shaped segment of the latch element would run in the groove NU. However, it is also possible that a latch tip, for example, engages into the groove NU of the lower part, similar to a transversal screw connection.

Figure 4B:
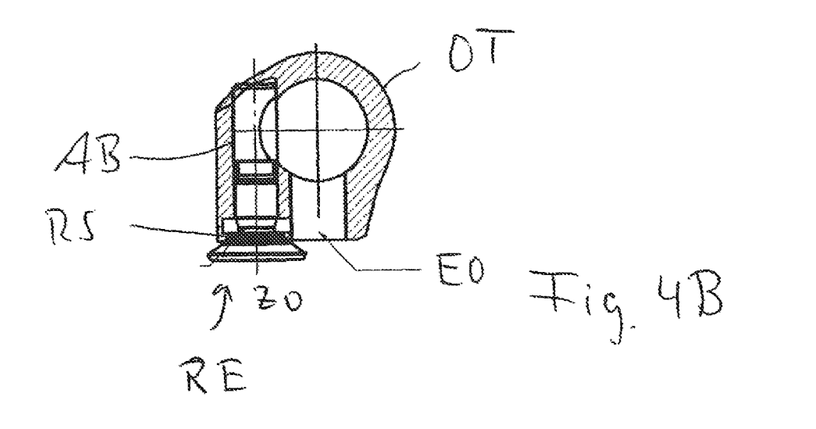

In FIG. 4(B), the latch element RE is shown once again in detail, in a top view. The latch element RE has the pin-shaped segment AB, wherein it is particularly provided that a reset element RS is configured in such a manner that the latch element RE remains in the engagement position.

In this regard, a latch element RE can be displaced in a latch accommodation oriented predominantly radially relative to the center axis MA, in the direction of a latch axis, between an engagement position shown in FIG. 4(B) and a release position moved away from the center axis MA in the direction of the latch axis. The latch element RE engages into the groove NU of the lower part UT with a latch tip on the pin-shaped segment AB, and, in this engagement position, prevents the upper part OT from being lifted off the lower part UT. The latch element is pressed in the direction of the center axis MA under the establishment of a spring force, and thereby maintains the engagement position on its own. In the advantageous example shown, the spring force is applied in that an elastically deformable ring lies in a groove in the upper part OT that surrounds the latch axis, which ring is supported in the groove to prevent displacement in the direction of the latch axis, and interacts with a conical surface over the course of the latch element RE, narrowing away from the latch tip, in such a manner that a force on the locking element in the direction toward the center axis MA occurs.

The ring can consist of elastic plastic material or also can exist as a metal ring, which can also be slit. A handle disposed outside of the latch guide allows manual retraction of the latch element RE from the engagement position shown in FIG. 4(B), and, accordingly, lifting of the upper part from the lower part. In this regard, the ring can be compressed by means of the said conical surface of the latch element and an increase in the reset force that acts on the latch element, or can be radially widened into a free space within the groove.

In a further embodiment, a U-shaped bracket locking mechanism, particularly a wire bracket having lateral bracket shanks that run tangentially with reference to the center axis MA and radially at a distance from the latter, and a center segment of the U-shaped bracket that connects the two lateral shanks, is provided. The bracket can preferably be displaced between a holding position and a release position, manually or by means of a tool. The lateral bracket shanks can also be formed in deviation from a straight shape, in order to lie against the groove NU with elastic bias, and thereby to prevent unintentional sliding out of engagement. In this embodiment, of course, the second opening ZO must be configured accordingly, in order to be able to accommodate the bracket.

As can be seen in FIG. 4(B), the latch element RE is thereby disposed within a second opening ZO, so that it can bring lower part UT and upper part OT into engagement. The second opening ZO can be disposed, for example, next to the first opening EO. This is particularly advantageous for the reason that in this way, a treating dentist can always access the dental prosthesis arrangement from the same side when selecting between an attachment means in the first opening EO and the second opening ZO. Within the scope of the invention, however, it is nevertheless possible to dispose the second opening, for example, at a 90° offset relative to the first opening, or opposite to it, or at any other desired locations of the upper part OT.

Figure 5:
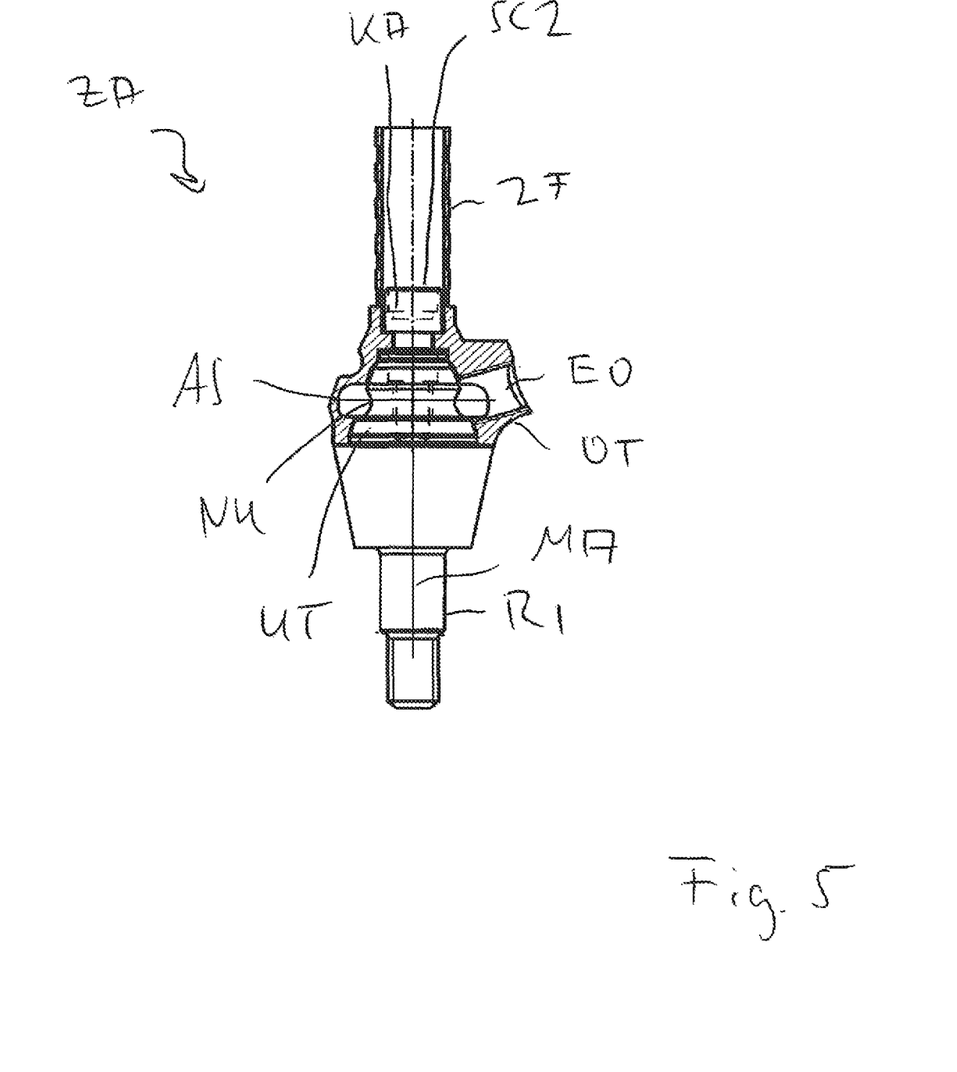

A further attachment possibility will be explained below, making reference to FIG. 5. The upper part of the embodiment shown in FIG. 5 is provided with a third opening DO at its top, which opening is surrounded by a cylindrical extension ZF, which is formed along the center axis MA. The third opening DO thereby in turn makes available a possibility for using a further element that passes through the upper part and stands in connection with the lower part for fixation. In this case, a further screw SC2 is provided, which is applied to the upper part OT from above, as what is called an occlusal screw connection, and connects the upper part OT and the lower part UT with one another by way of a corresponding inside thread in the lower part UT. The second opening ZO and/or the first opening EO can be closed off, once again, as was already explained above, in the case of an occlusal screw connection, wherein it is also not necessary to affix the holding element between groove NU and recess AS, because upper part OT and lower part UT are now connected by way of the further screw SC2.

Accordingly, the dental prosthesis arrangement according to the invention makes many different attachment means available, which can be selected depending on the application case, in order to make the optimal property available for the patient, in each instance when attaching upper part OT to lower part UT. All of these attachment means have in common that they can be released, so that the wearer of the dental prosthesis or a treating dentist can perform cleaning of the dental prosthesis arrangement ZA at regular intervals. In view of the implications mentioned initially, of the biofilm that is frequently present on dental prosthesis arrangements, this possibility is particularly important for maintaining the health of the patient.

The embodiments described until now in connection with FIG. 1 to 5 have the cylindrical extension ZF on the top side, i.e. the side facing away from the jaw implant PI, in each instance. However, it is also possible to configure the top side of the upper part OT in closed manner, so that the upper part OT is configured in the form of a cap. The closed surface is indicated with the broken line in FIG. 5, as the cap KA.

A further embodiment of the invention is shown in FIG. 6. Here, the cylindrical extension ZF is inclined relative to the center axis MA. The cylindrical extension ZF and the upper part OT, together with the occlusal screw connection by means of the screw SC2, can be structured in one piece, for example by way of a weld. Accordingly, the further screw SC2 is formed as a captive screw. A captive screw can also be implemented in the embodiments shown as FIGS. 1 to 5.

The dental prosthesis arrangement according to FIG. 6 makes it possible to displace the cylindrical extension ZF that usually passes through the dental prosthesis and thereby forms a passage opening to a lateral position of the dental prosthesis, so that lower chewing forces, for example, can be in effect at that location. This makes it possible to be able to guarantee longer durability of the dental prosthesis.

In a further embodiment, the cylindrical extension ZF is provided with a thread GE along its outer wall AW or inner wall IW, onto which thread the dental prosthesis can be screwed. Consequently, a connection of the dental prosthesis superstructure with the dental prosthesis arrangement ZA is created, which connection can be implemented in simple and flexible manner. The thread GE can also be implemented in the embodiments shown in FIGS. 1 to 5.

The holding element HE, the latch element RE, and the transversal screw connection by means of the screw SC, as well as the occlusal screw connection by means of the further screw SC2, bring about an axial press-down force against a contact surface at the end of the connection segment between upper part OT and lower part UT that faces the jaw implant.

The characteristics indicated above and in the claims, as well as those that can be derived from the figures, can be advantageously implemented both individually and in different combinations. The invention is not restricted to the exemplary embodiments described, but rather can be modified in many ways, within the scope of the ability of a person skilled in the art.

The invention claimed is:

1. A dental prosthesis system for connection of at least one jaw implant with a superstructure, the dental prosthesis system comprising:
    a lower part assigned to the jaw implant,
    an upper part assigned to the superstructure, and
    a first holding element, a second holding element, and a third holding element,
    wherein the lower part engages into the upper part along a center axis,
    wherein the lower part is supported against the upper part at multiple contact surfaces,
    wherein the lower part comprises a ring-shaped groove directed radially inward,
    wherein the upper part comprises a recess directed radially outward and an occlusal screw opening, the recess corresponding to the ring-shaped groove of the lower part,
    wherein the upper part further comprises:
        a transverse opening configured cylindrically, provided with an inside thread, and running along a line intersecting the center axis, or
        a tangential opening arranged tangentially with respect to a common center axis of the upper part and the lower part,
    wherein at least a first attachment possibility, a second attachment possibility, and a third attachment possibility are provided,
    wherein each of the first, the second, and the third attachment possibility is able to bring about a holding force that prevents the upper part from being axially pulled off the lower part using the first, the second, or the third holding element, respectively,
    wherein only one of the first, the second, and the third attachment possibilities is selected at a particular time,
    wherein the first attachment possibility uses a ring or a string as the first holding element, the ring or the string being provided between the ring-shaped groove and the recess,
    wherein the second attachment possibility uses:
        a screw as the second holding element, the screw being undertaken through the transverse opening and being brought into engagement with the ring-shaped groove, or
        a latch element as the second holding element, the latch element projecting through the tangential opening on the upper part and being brought into engagement with the ring-shaped groove, and
    wherein the third attachment possibility uses an occlusal screw as the third holding element, the occlusal screw being undertaken through the occlusal screw opening and being brought into engagement with an inside thread in the lower part.

2. The dental prosthesis system according to claim 1, wherein the ring comprises a rubber-elastic and/or elastically compressible material, and
    wherein the ring is configured to be elastically deformed radially.

3. The dental prosthesis system according to claim 1,
    wherein the latch element comprises a pin-shaped segment and a latch tip, and
    wherein the latch tip is configured to engage into the ring-shaped groove in an engagement position.

4. The dental prosthesis system according to claim 3, wherein the latch element is configured as an insertion latch, sliding latch, pivot latch, rotating latch or U-shaped bracket locking mechanism.

5. The dental prosthesis system according to claim 1, wherein the occlusal screw opening is an upward opening.

6. The dental prosthesis system according to claim 5, wherein the occlusal screw opening is surrounded by a cylindrical extension, which faces away from the lower part.

7. The dental prosthesis system according to claim 6, wherein the cylindrical extension is formed in a direction of the center axis.

8. The dental prosthesis system according to claim 6, wherein the cylindrical extension is angled relative to the center axis.

9. The dental prosthesis system according to claim 6, wherein the cylindrical extension and the upper part are structured in one piece or are welded to one another.

10. The dental prosthesis system according to claim 6, wherein the cylindrical extension is provided with a thread along its outer wall or inner wall, at least in certain sections.

11. The dental prosthesis system according to claim 1, wherein the holding force can be overcome without destruction of the upper part and the lower part, in order to release a connection between the upper part and the lower part.

12. The dental prosthesis system according to claim 11, wherein the holding force can be overcome without destruction of the respective first, second, or third holding element.

* * * * *